United States Patent [19]
Hofmann et al.

[11] Patent Number: 5,972,034
[45] Date of Patent: Oct. 26, 1999

[54] SELF-VENTING INTRAMEDULLARY CEMENT RESTRICTOR

[75] Inventors: Aaron A. Hofmann, Salt Lake City, Utah; Charles H. Perrone, Jr., Austin, Tex.

[73] Assignee: Joint Enterprises, L.C. a Limited Corporation

[21] Appl. No.: 09/124,387

[22] Filed: Jul. 28, 1998

Related U.S. Application Data

[60] Provisional application No. 60/054,133, Jul. 29, 1997.

[51] Int. Cl.⁶ ........................................................ A61F 2/30
[52] U.S. Cl. .................................. 623/23; 623/16; 606/95
[58] Field of Search .......................... 623/23, 18; 606/92, 606/95, 93

[56] References Cited

U.S. PATENT DOCUMENTS

| | | |
|---|---|---|
| 2,550,866 | 5/1951 | Rosan . |
| 2,562,419 | 7/1951 | Ferris . |
| 3,793,650 | 2/1974 | Ling et al. . |
| 4,175,555 | 11/1979 | Herbert . |
| 4,245,359 | 1/1981 | Stuhmer . |
| 4,262,665 | 4/1981 | Roalstad et al. . |
| 4,276,659 | 7/1981 | Hardinge . |
| 4,293,962 | 10/1981 | Fuson . |
| 4,302,855 | 12/1981 | Swanson . |
| 4,344,190 | 8/1982 | Lee et al. . |
| 4,447,915 | 5/1984 | Weber . |
| 4,523,587 | 6/1985 | Frey . |
| 4,686,973 | 8/1987 | Frisch . |
| 4,697,584 | 10/1987 | Haynes . |
| 4,870,957 | 10/1989 | Goble et al. . |
| 5,078,746 | 1/1992 | Garner . |
| 5,100,405 | 3/1992 | McLaren . |
| 5,116,336 | 5/1992 | Frigg . |
| 5,192,283 | 3/1993 | Ling et al. . |
| 5,197,989 | 3/1993 | Hinckfuss et al. . |
| 5,290,318 | 3/1994 | Ling et al. . |
| 5,340,362 | 8/1994 | Carbone . |
| 5,376,120 | 12/1994 | Sarver et al. . |
| 5,383,932 | 1/1995 | Wilson et al. . |
| 5,403,136 | 4/1995 | Mathys . |
| 5,560,248 | 10/1996 | Mathews . |
| 5,662,657 | 9/1997 | Carn . |
| 5,782,917 | 7/1998 | Carn . |
| 5,877,178 | 6/1998 | Michielli et al. ........................ 606/95 |

FOREIGN PATENT DOCUMENTS

| | | |
|---|---|---|
| 0006408 | 11/1978 | European Pat. Off. . |
| 0434604 | 11/1990 | European Pat. Off. . |
| 4136317 | 5/1993 | Germany . |
| 2211741 | 7/1989 | United Kingdom . |

OTHER PUBLICATIONS

Allpro—Stuhmer/Weber Medullary Plugs With Drain K57e ed. Jul. 1993; K56e.Ed. Jul. 1993; K58e–Ed. Aug. 1993
Corin—The Corin Total and Hemi Hip Solution.

*Primary Examiner*—David H. Willse
*Assistant Examiner*—Suzette J. Jackson
*Attorney, Agent, or Firm*—Kelly Bauersfeld Lowry & Kelley, LLP

[57] ABSTRACT

A self-venting cement restrictor or bone plug is provided for insertion into the medullary canal of a patient bone during orthopedic surgery. The cement restrictor includes a valve member which accommodates passage of air and body fluids therethrough as the cement restrictor is placed to avoid pressurizing the downstream medullary space. An installation tool is manipulated in the course of cement restrictor installation for shifting the valve member to a closed position, whereby the cement restrictor retains bone cement introduced subsequently under pressure within the upstream medullary space.

18 Claims, 2 Drawing Sheets

SELF-VENTING INTRAMEDULLARY CEMENT RESTRICTOR

This application claims benefit of Provisional Appln. 60/054,133 filed Jul. 29, 1997.

BACKGROUND OF THE INVENTION

This invention relates generally to improvements in devices and procedures for artificial joint replacement (arthroplasty). More specifically, this invention relates to an improved intramedullary cement restrictor or bone plug for confining or restricting the placement of bone cement introduced under pressure into the medullary canal of a patient bone during arthroplasty surgery, such as a hip joint replacement.

Artificial or prosthetic joint structures are used extensively to repair or replace a patient joint, such as hip, knee and shoulder joints. The prosthesis typically comprises a biocompatible structure or structures such as a titanium or cobalt-chrome alloy with a size and shape for secure affixation to a surgically resected patient bone. In many cases, the prosthetic device includes an elongated stem for slide-fit placement into the exposed medullary canal of the resected patient bone, such as the upper end of a patient's femur in the case of a hip replacement. A bone cement, typically methyl methacrylate, is often introduced under pressure into the medullary canal to provide a positive and stable prosthesis attachment to the patient bone. The pressurized bone cement is intended to fill the interstices of bone structure in surrounding relation to the prosthetic device to result in optimum prosthesis fixation.

When pressurized bone cement is introduced into the medullary canal, it is necessary or desirable to use a restrictor or plug element to confine the cement to surrounding relation with the prosthesis, rather than to permit the bone cement to migrate distally through the medullary canal in a direction away from the prosthesis. In this regard, numerous restrictor or plug devices have been developed for this purpose, and are adapted to be installed into the medullary canal immediately prior to placement of the prosthesis and bone cement. However, such prior restrictor or plug devices have generally comprised solid structural bodies which tend to compress air within the medullary canal at the downstream side thereof during slide-fit placement. Such compression of air within the downstream medullary space can result in undesirable and potentially dangerous embolisms.

There exists, therefore, a significant need for further improvements in cement restrictors for use in orthopedic surgery, particularly wherein a cement restrictor is designed to vent the downstream medullary space during placement thereof, and thereafter to accommodate facilitated sealing of the vent path to maintain pressurized bone cement within the upstream medullary space. The present invention fulfills these needs and provides further related advantages.

SUMMARY OF THE INVENTION

In accordance with the invention, an improved self-venting cement restrictor or bone plug is provided for placement into the medullary canal of a patient bone during orthopedic surgery, such as hip replacement surgery. The cement restrictor includes a hollow and generally cylindrical body with a valve member therein in a normally open position defining an open vent path. The cement restrictor is installed into the medullary canal with the valve member in the open position, thereby venting the downstream medullary space. When the cement restrictor is fully installed, the valve member is movable to a closed position sealing the vent path, thereby maintaining subsequently introduced pressurized bone cement within the upstream medullary space.

In the preferred form, the cylindrical body is constructed from a lightweight biocompatible material such as polyethylene or the like, to include one or more outwardly radiating fins having a size and shape for securely engaging the walls of the medullary space when the cement restrictor is inserted to the desired final position. An installation tool is provided for releasible connection, as by threaded connection, with the cylindrical body for placement thereof into the medullary canal. The installation tool defines an open vent path leading from the hollow interior of the cylindrical body for venting the downstream medullary space.

When the cement restrictor is installed in the desired position along the length of the medullary canal, the installation tool is adapted for manipulation relative to the cylindrical body to displace the valve member from the open position to the closed position. In the preferred form, the valve member comprises a valve ball adapted for snap-fit displacement within the cylindrical body to the closed position.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 2:
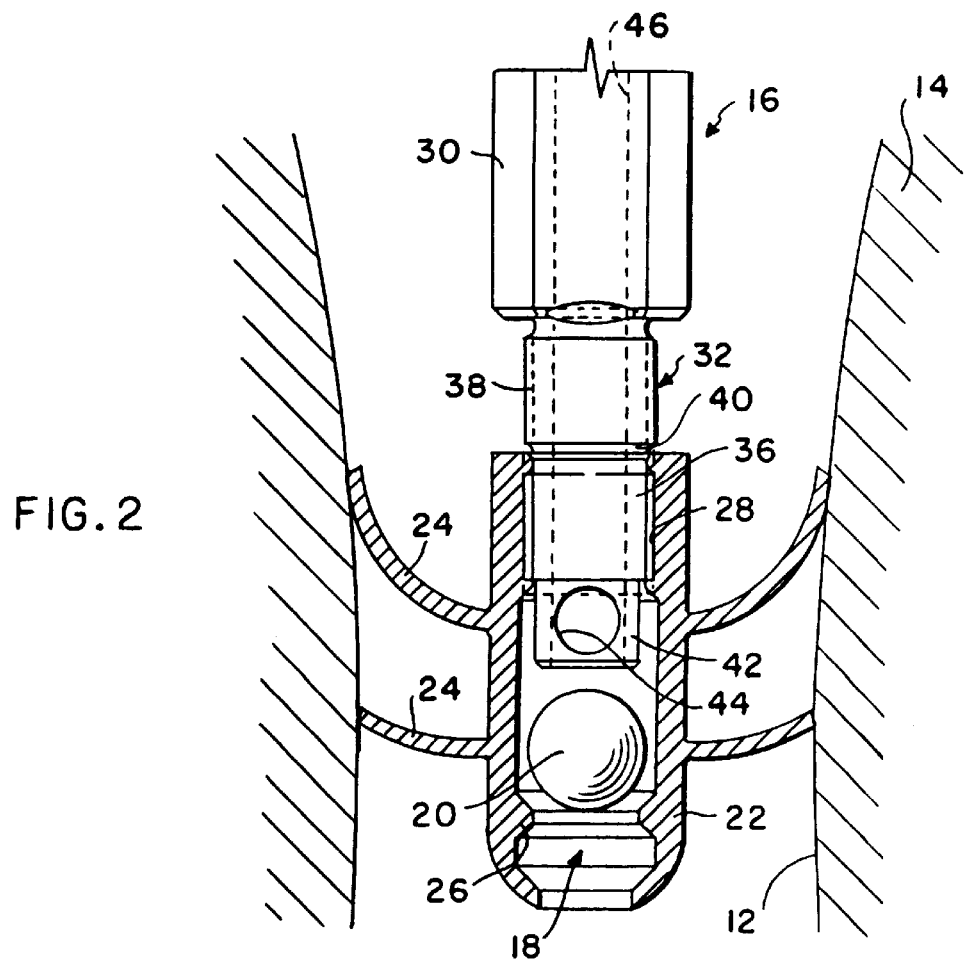
FIG. 2 is a vertical sectional view showing the cement restrictor of FIG. 1 in assembled relation with a related installation tool, and placed into the medullary canal of a patient bone.
Figure 3:
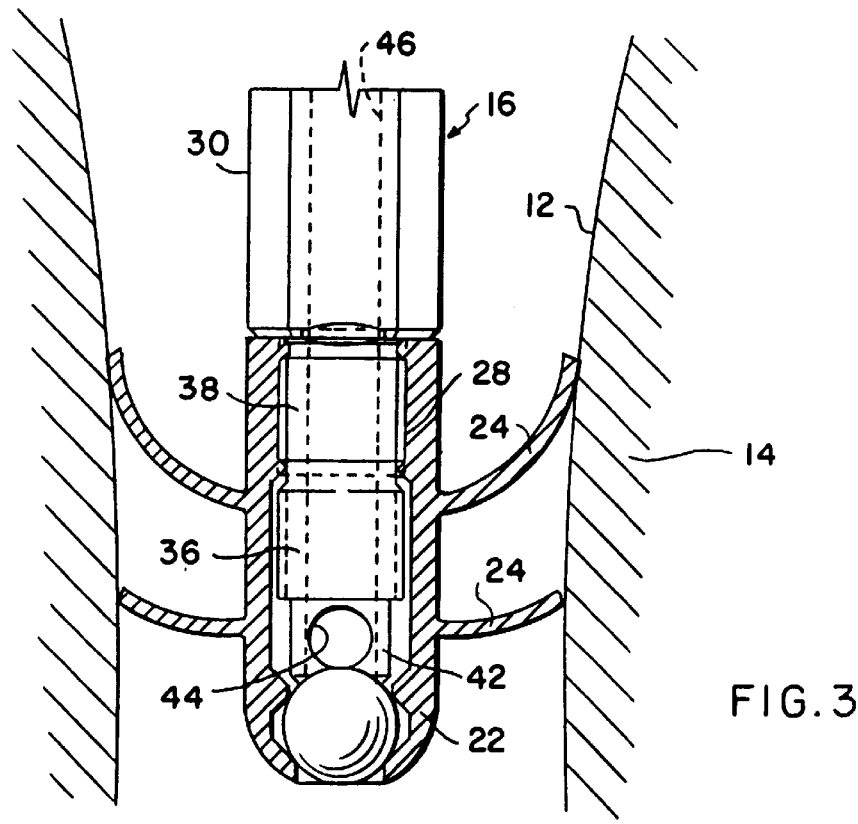
FIG. 3 is a vertical sectional view illustrating the assembled cement restrictor and installation tool, with the cement restrictor placed into the medullary canal of a patient bone and the installation tool manipulated to displace a valve member for closing and sealing a vent path through the cement restrictor.
Figure 4:
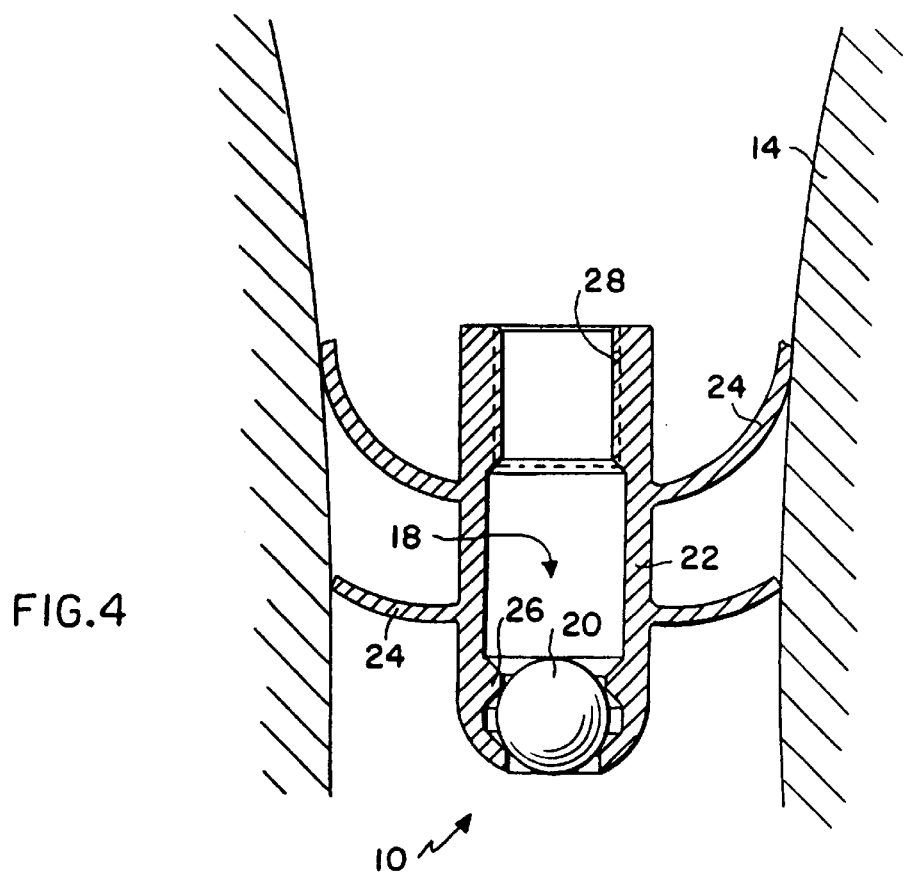
FIG. 4 is a vertical sectional view showing the cement restrictor installed within the medullary canal following separation of the installation tool therefrom.

As shown in the exemplary drawings, an improved self-venting cement restrictor referred to generally by the reference numeral 10 is provided for placement into the medullary canal 12 of a patient bone 14 (FIGS. 2–4), by means of an installation tool 16 (FIGS. 2–4). The cement restrictor 10 and associated installation tool 16 cooperatively define a vent path 18 for venting the downstream medullary space during installation of the cement restrictor 10 into the medullary canal 12. Following seated installation of the cement restrictor 10, a valve member 20 is adapted for movement to a closed and sealed position to confine and retain bone cement introduced under pressure into the upstream medullary space.

The cement restrictor 10 comprises a generally cylindrical body 22 of hollow construction formed from a suitable biocompatible material such as polyethylene or the like, preferably in the form of a one-piece component. The cylindrical body 22 has a blunted or tapered nose end for facilitated and self-guiding slide-fit placement into the medullary canal 12 of a resected patient bone, such as into the upper end of a femur in the course of hip replacement surgery. At least one and preferably a plurality of outwardly radiating fins 24 are formed on the cylindrical body 22 for sealingly engaging the interior wall of the medullary canal 12. The hollow interior of the cylindrical body 22 defines the vent path 18 which permits air to flow through the cement restrictor from the downstream to the upstream side thereof, as the cement restrictor is slide-fit placed into the medullary canal 12.

Figure 1:
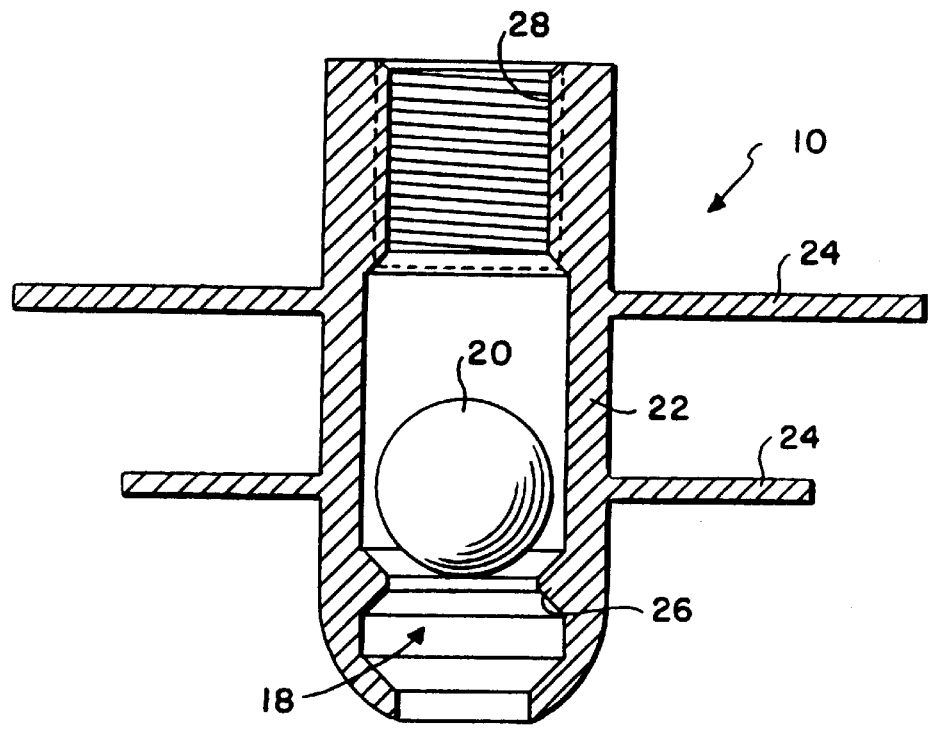
FIG. 1 is a vertical sectional view showing the improved cement restrictor embodying the novel features of the invention.

The valve member 20 is shown in the form of a valve ball captured within the vent path 18, in the interior of the cylindrical body 22. In a normal or open position as viewed in FIGS. 1 and 2, the valve ball 20 is relatively loosely retained in a floating manner within a relatively large central cavity defined between an inwardly radiating rib 26 at the downstream side and an internally threaded segment 28 at the upstream side. The valve ball 20 is designed for forced snap-fit displacement in a downstream direction past the rib 26 to a closed position (FIGS. 3 and 4) received tightly and sealingly between the rib 26 and the nose end of the body 22. In the closed position, fluid flow through the vent path 18 is prevented.

The installation tool 16 is shown in more detail in FIGS. 2 and 3. As shown, the installation tool 16 comprises an elongated tool shank 30 having a distal or tip end 32 joined to a tool tip of reduced diametric size. The tool tip is shown in the preferred form to comprise a pair of externally threaded segments 36 and 38 with an annular groove or recess 40 disposed axially therebetween. A cap segment 42 protrudes axially beyond the threaded segments 36 and 38 and includes a cross bore 44 which intersects and thus communicates with an elongated central passage 46 formed through the installation tool 16.

The installation tool 16 is assembled with the cement restrictor 12 prior to placement of the cement restrictor into the medullary canal of the patient bone. This initial assembly is shown in FIG. 2, with the leading threaded segment 36 rotatably engaged with the internally threaded segment 28 at the proximal end of the restrictor body 22. In this position, the valve ball 20 is contained between the cap segment 42 and the rib 26 for relatively free floating movement therein. The groove 40 between the threaded segments 36 and 38 is exposed at the proximal end of the restrictor 10 to provide a visual indication that the valve ball 20 is in the open position.

The installation tool 16 is then employed for slide-fit placement of the cement restrictor 10 to a desired position along the length of the medullary canal 12, as viewed in FIG. 3. During such placement, the fins 24 typically deflect so that their outer edges are turned in an upstream or proximal direction, but are otherwise engaged and sealed with the interior wall defining the medullary canal 12. Importantly, during such placement of the cement restrictor 10, air and other body fluids within the downstream medullary space is vented through the vent path 18 and the central passage 46, to avoid pressurizing the downstream medullary space. In this regard, such venting is positively maintained even if the ball valve 20 seats against the tool tip 34, by virtue of the cross bore 44 in flow communication with the tool passage 46.

When the cement restrictor 10 is placed in the desired final position along the length of the medullary canal, the installation tool 16 is manipulated to displace the valve ball 20 from the open position (FIG. 2) to the closed position (FIGS. 3 and 4). More particularly, the tool tip 32 is threadably advanced within the threaded segment 28 to engage and force the valve ball 20 past the rib 26 to the closed and sealed position. The installation tool 16 can then be threadably disengaged from the cement restrictor 10 and withdrawn from the medullary canal 12, leaving the cement restrictor in place with the ball valve 20 in the closed and sealed position as viewed in FIG. 4. Thereafter, the cement restrictor functions to retain bone cement under pressure within the upstream medullary space, without bypass leakage thereof to the downstream space.

A variety of further modifications and improvements to the cement restrictor 10 of the present invention will be apparent to those skilled in the art. Accordingly, no limitation on the invention is intended by way of the foregoing description and accompanying drawings, except as set forth in the appended claims.

What is claimed is:

1. An intramedullary cement restrictor for placement into the medullary canal of a patient bone, said cement restrictor comprising:

a generally cylindrical hollow body having a size and shape for reception into the medullary canal of a patient bone, said body defining a vent path positioned to enable the passage of fluid therethrough upon insertion thereof into the medullary canal to prevent pressurization of the medullary canal at a downstream side of said body; and a valve member within said vent path, said valve member being movable between an open position permitting passage of fluid through said vent path upon insertion of said body into the medullary canal, and a closed position to substantially close said vent path following insertion of said body into the medullary canal.

2. The cement restrictor of claim 1 further including at least one outwardly radiating fin for sealingly engaging the patient bone lining the medullary canal upon insertion of said body into the medullary canal.

3. The cement restrictor of claim 1 wherein said body is formed from a biocompatible plastic material.

4. The cement restrictor of claim 1 wherein said valve member comprises a valve ball, said body having at least one inwardly radiating rib formed along said vent path, said valve ball being movable past said rib with a snap action from said open position to said closed position.

5. The cement restrictor of claim 1 wherein said body has a tapered nose end for facilitated self-guiding slide-fit reception into the medullary canal.

6. The cement restrictor of claim 5 wherein said body further includes an internally threaded section formed at an upstream end thereof generally opposite to said nose end.

7. The cement restrictor of claim 6 further including an installation tool removably connected to said internally threaded section of said body, said installation tool including means for displacing said valve member from said open position to said closed position.

8. The cement restrictor of claim 6 wherein said installation tool includes an externally threaded distal tip for threaded connection with said internally threaded section of said body, said threaded distal tip including first and second threaded segments separated axially by a groove, said first threaded segment being engaged with said body and with said groove exposed at the upstream end of said body upon insertion of said body into the medullary canal with said valve member in said open position, and said valve member being displaced from said open position to said closed position upon advancement of said installation tool for engaging said second threaded segment with said body.

9. The cement restrictor of claim 1 further including an installation tool removably connected to said body, said installation tool including means for displacing said valve member from said open position to said closed position.

10. The cement restrictor of claim 9 wherein said installation tool has a central passage formed therein for venting said vent path in said body upon installation of said body into the medullary canal.

11. An intramedullary cement restrictor for placement into the medullary canal of a patient bone, said cement restrictor comprising:

a generally cylindrical hollow body formed from a biocompatible plastic material and having a size and shape for reception into the medullary canal of a patient bone, said body defining a tapered nose end for facilitated insertion into the medullary canal, said body further defining a vent path positioned to enable the passage of fluid therethrough upon insertion thereof into the medullary canal to prevent pressurization of the medullary canal at a downstream side of said body;

at least one outwardly radiating fin on said body for sealingly engaging the patient bone lining the medullary canal upon insertion of said body into the medullary canal; and a valve member within said vent path, said valve member being movable between an open position permitting passage of fluid through said vent path upon insertion of said body into the medullary canal, and a closed position to substantially close said vent path following insertion of said body into the medullary canal.

12. The cement restrictor of claim 11 wherein said valve member comprises a valve ball, said body having at least one inwardly radiating rib formed along said vent path, said valve ball being movable past said rib with a snap action from said open position to said closed position.

13. The cement restrictor of claim 11 wherein said body further includes an internally threaded section formed at an upstream end thereof generally opposite to said nose end.

14. The cement restrictor of claim 13 further including an installation tool removably connected to said internally threaded section of said body, said installation tool including means for displacing said valve member from said open position to said closed position.

15. The cement restrictor of claim 13 wherein said installation tool includes an externally threaded distal tip for threaded connection with said internally threaded section of said body, said threaded distal tip including first and second threaded segments separated axially by a groove, said first threaded segment being engaged with said body and with said groove exposed at the upstream end of said body upon insertion of said body into the medullary canal with said valve member in said open position, and said valve member being displaced from said open position to said closed position upon advancement of said installation tool for engaging said second threaded segment with said body.

16. The cement restrictor of claim 11 further including an installation tool removably connected to said body, said installation tool including means for displacing said valve member from said open position to said closed position.

17. The cement restrictor of claim 16 wherein said installation tool has a central passage formed therein for venting said vent path in said body upon installation of said body into the medullary canal.

18. An intramedullary cement restrictor for placement into the medullary canal of a patient bone, said cement restrictor comprising:

a generally cylindrical hollow body formed from a biocompatible plastic material and having a size and shape for reception into the medullary canal of a patient bone, said body defining a tapered nose end for facilitated insertion into the medullary canal, said body further defining a vent path for passage of fluid therethrough upon insertion thereof into the medullary canal to prevent pressurization of the medullary canal at a downstream side of said body;

at least one outwardly radiating fin on said body for sealingly engaging the patient bone lining the medullary canal upon insertion of said body into the medullary canal; and a valve ball within said vent path, said valve ball being movable between an open position permitting passage of fluid through said vent path upon insertion of said body into the medullary canal, and a closed position to substantially close said vent path following insertion of said body into the medullary canal, said body having at least one inwardly radiating rib formed along said vent path, said valve ball being movable past said rib with a snap action from said open position to said closed position.

* * * * *